Figure 1:
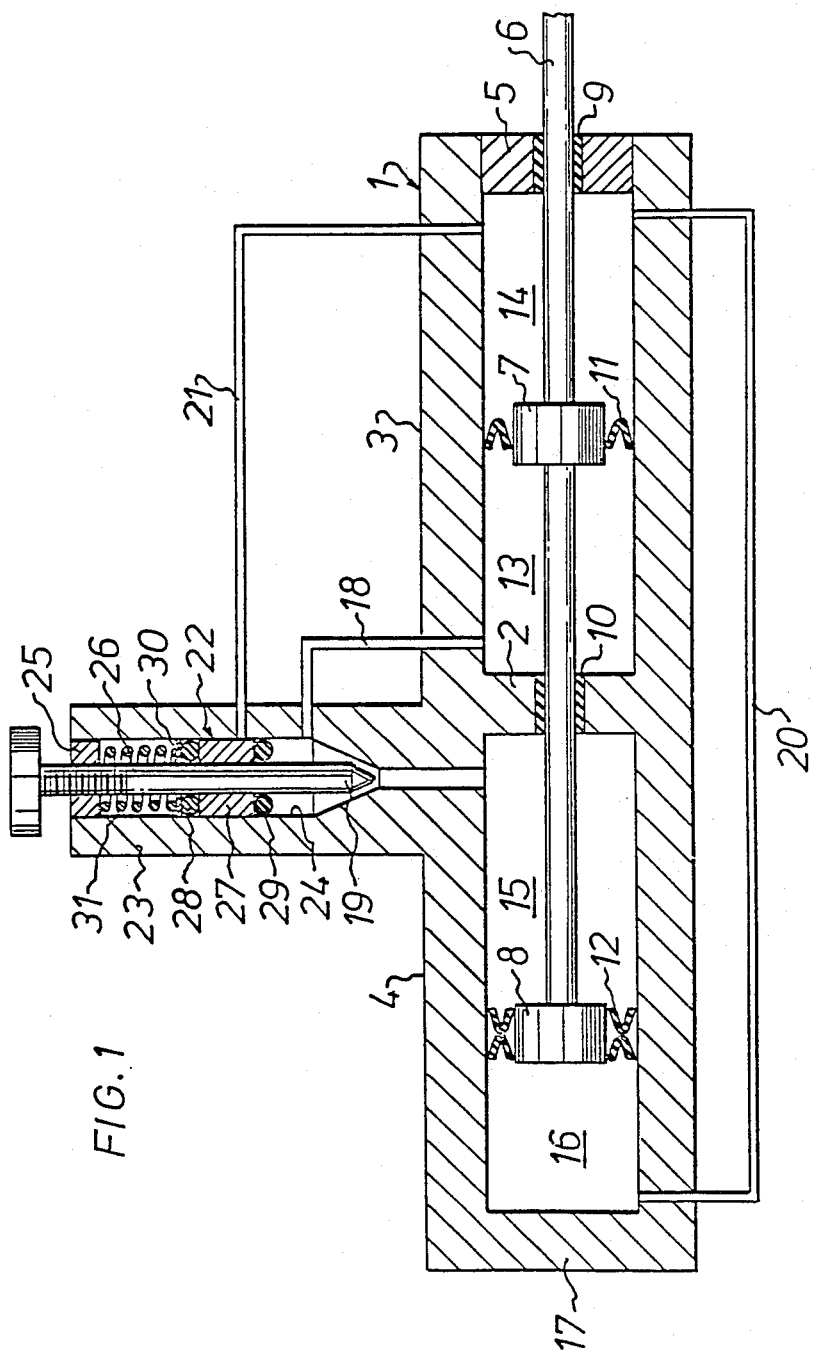

United States Patent [19]

Stenberg

[11] Patent Number: 4,775,037

[45] Date of Patent: Oct. 4, 1988

[54] HYDRAULIC DEVICE

[75] Inventor: Karl-Erik Stenberg, Växjö, Sweden

[73] Assignee: Vaxjo-Protes AB, Växjö, Sweden

[21] Appl. No.: 929,426

[22] Filed: Nov. 12, 1986

Related U.S. Application Data

[62] Division of Ser. No. 826,833, Feb. 6, 1986, Pat. No. 4,662,486.

[30] Foreign Application Priority Data

Feb. 18, 1985 [SE] Sweden ............................ 8500740

[51] Int. Cl.$^4$ .............................................. F16F 9/20
[52] U.S. Cl. ........................................ 188/312; 16/56; 188/316; 188/318; 188/322.15; 623/39
[58] Field of Search ............... 188/312, 313, 316, 317, 188/318, 322.15, 322.18; 267/129, 64.25; 16/56; 623/26, 39

[56] References Cited

U.S. PATENT DOCUMENTS

| | | | |
|---|---|---|---|
| 1,273,059 | 7/1918 | Hild | 188/312 |
| 2,029,829 | 2/1936 | Messier | 188/312 |
| 2,497,972 | 2/1950 | Beecher | 188/316 |
| 2,543,908 | 3/1951 | Guzey | 623/26 |
| 2,715,389 | 8/1955 | Johnson | 188/313 X |
| 2,912,069 | 11/1959 | Dillenburger | 188/322.18 X |
| 3,176,801 | 4/1965 | Huff | 188/313 X |
| 3,670,341 | 6/1972 | Webb et al. | 188/322.19 X |
| 4,099,602 | 7/1978 | Kourbetsos | 188/312 X |

FOREIGN PATENT DOCUMENTS 2529624 1/1984 France.

Primary Examiner—George E. A. Halvosa
Attorney, Agent, or Firm—Bacon & Thomas

[57] ABSTRACT

A hydraulic device for controlling the knee-joint function in a leg prosthesis has a cylinder which is divided into first and a second cylinder parts adapted to be fixed to the lower leg of the prosthesis, and a piston rod which carries one piston in each cylinder part and is fixed to the upper leg of the prosthesis. The pistons divide the interior of the respective cylinder parts into two chambers. The adjacent first chambers of the cylinder parts are interconnected by a throttle device. The two, second chambers are also interconnected. One piston has a sealing member which is of a single-acting type to allow leakage of hydraulic fluid from the second chamber to the first chamber when the piston is moved in a direction reducing the volume of the second chamber, while it is completely sealing when the piston is moved in the opposite direction. A connection is provided between one of the first chambers and one of the second chambers. A pressure relief valve is arranged for opening this connection when the pressure of the hydraulic fluid in the one first chamber exceeds a predetermined value.

3 Claims, 2 Drawing Sheets

HYDRAULIC DEVICE

This application is a division of application Ser. No. 826,833, filed on 2-6-86, now U.S. Pat. No. 4,662,486.

The present invention relates to a hydraulic device which has a cylinder containing hydraulic fluid and having an internal transverse partition which divides the cylinder into a first cylinder part and a second cylinder part, and a piston rod extending into said first cylinder part through the end wall thereof and further into said second cylinder part through said transverse partition and carrying a first piston and a second piston, said pistons being disposed in said first and said second cylinder part, respectively, and being sealed with respect thereto by sealing means and dividing the interior of the respective cylinder part into a first chamber between the piston and said transverse partition, and a second chamber between the piston and the end wall of the respective cylinder part, both of said first chambers communicating with each other through a first connecting line containing throttle means, and both of said second chambers communicating with each other through a second connecting line, which hydraulic device is adapted, with said piston rod, to be fixed to a first part, such as the upper leg of a leg prosthesis, and with said cylinder to a second part, such as the lower leg of said leg prosthesis, which is movable with respect to said first part of the prosthesis, in order to dampen the movements of said two prosthetic parts in relation to each other.

Prior art hydraulic devices of this type are used in leg prostheses for controlling the functions of the knee-joint. In this context, they are used for controlling the stand phase, i.e. the phase of a step in which the foot is in contact with the ground, and the swing phase, i.e. the phase of a step in which the foot is not in contact with the ground, but is either moving backwards (bending of the knee-joint) or moving forwards (stretching of the knee-joint). In addition to the above-mentioned components, a hydraulic device used for controlling the knee-joint functions in a leg prosthesis often has special mechanisms and valve arrangements making the device especially well suited for such use. One example hereof is a valve which is adapted, in some phases of motion of the leg prosthesis, to completely close the connection between the two first chambers in order to lock the piston rod and, hence, the upper leg and the lower leg of the prosthesis with respect to each other.

If the sealing means between the pistons and the cylinder wall have been worn or, for some reason or other, are not completely sealing, there will be obtained in the two first chambers, either a pressure increase making the dampening of the hydraulic device relatively unelastic, or a pressure decrease with ensuing cavitation, which makes the dampening, when it should be unelastic and bring about mutual locking of the two parts of the prosthesis, give an undesired elasticity.

The object of the present invention is to provide a hydraulic device which is especially well suited for use in a leg prosthesis and which obviates the above-mentioned shortcoming.

According to the invention, this object is achieved by means of a hydraulic device which is of the type described in the introduction to this specification and which is characterized in that the sealing means of at least one piston is of such a single-acting type as to permit leakage of hydraulic fluid from the respective second chamber to the respective first chamber when the piston rod is moved in a direction away from said transverse partition, while it is completely sealing when the piston rod is moved in the opposite direction, and that a connection is provided between one of said first chambers and one of said second chambers, pressure relief valve means being provided for opening said connection when the pressure of the hydraulic fluid in said one first chamber exceeds a predetermined value.

In a preferred embodiment, the single acting sealing means is a U-gasket the open portion of which is facing the transverse partition.

Figure 2:
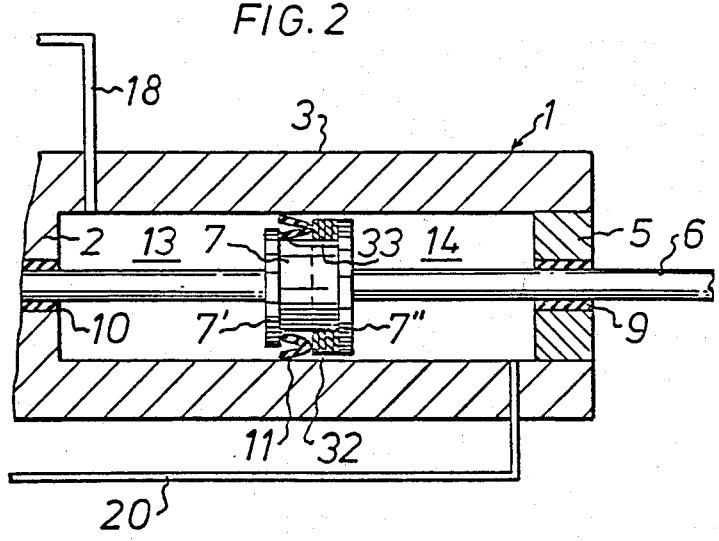

The invention will now be described in greater detail hereinbelow with reference to the accompanying drawings, in which:

FIG. 1 is a schematic longitudinal section of a hydraulic device according to the present invention; and FIG. 2 illustrates an alternative piston-seal arrangement.

The hydraulic device schematically illustrated in FIG. 1 has a cylinder 1 containing hydraulic fluid. The cylinder 1 is divided by an internal transverse partition 2 into a first cylinder part 3 and a second cylinder part 4. The end wall 5 of the first cylinder part 3 consists of a plug screwed in one end of the cylinder 1. A piston rod 6 extends through the end wall 5 into the first cylinder part 3 and further through the internal transverse partition 2 into the second cylinder part 4. The piston rod 6 carries a first piston 7 in the first cylinder part 3 and a second piston 8 in the second cylinder part 4. The piston rod 6 is sealed with respect to the end wall 5 by means of a seal 9 and with respect to the internal transverse partition 2 by means of a seal 10. The first piston 7 is sealed with respect to the inner wall of the first cylinder part 3 by sealing means 11, and the second piston 8 is sealed with respect to the inner wall of the second cylinder part 4 by sealing means 12.

The hyrualic device is especially well suited for use in controlling the knee-joint functions of a leg prosthesis. To this end, the piston rod 6 should be fixed to the upper leg of the prosthesis, and the cylinder 1 should be fixed with the second cylinder part 4 to the lower leg of the prosthesis.

The first piston 7 divides the interior of the first cylinder part 3 into a first chamber 13 between the piston 7 and the internal transverse partition 2, and a second chamber 14 between the piston 7 and the end wall 5. Similarly, the second piston 8 divides the interior of the second cylinder part 4 into a first chamber 15 between the piston 8 and the internal transverse partition 2, and a second chamber 16 between the piston 8 and the end wall 17 of the second cylinder part 4.

The first chambers 13 and 15, which are completely filled with hydraulic fluid, communicate with each other by a first connecting line 18 which accomodates throttle means 19, and the second chambers 14 and 16, also containing hydraulic fluid, communicate with each other through a second connecting line 20. The cylinder 1 is not connected to an external hydraulic fluid source and, thus, has two closed hydraulic fluid systems, namely a first system comprising the chambers 13 and 15 and the connecting line 18, and a second system comprising the chambers 14 and 16 and the connecting line 20.

When the piston rod 6 is withdrawn from the cylinder 1, the volume of the first chamber 15 of the second cylinder part 4 decreases, while the volume of the first chamber 13 of the first cylinder part 3 increases correspondingly. Hydraulic fluid in the chamber 15 will then be pressed through the connecting line 18 over to the chamber 13, the throttle means 19 exerting a throttling action on the flow of hydraulic fluid, whereby the movement of the piston rod 6 will be dampened. When the piston rod 6 is moved into the cylinder 1, the hydraulic fluid will be pressed in the opposite direction.

In order, when the hydraulic device is used in a leg prosthesis, to make it easier to stretch the leg prosthesis than to bend it, it is possible, in the connecting line 18 in parallel with the throttle means 19, to provide a nonreturn valve which is so arranged that the flow of hydraulic fluid is throttled when flowing in the direction from the chamber 15 to the chamber 13 whereas not in the opposite direction. In either of the first chambers 13 and 15, it is also possible to provide an externally operable valve arrangement making it possible to lock the piston rod 6 and, hence, the upper leg and the lower leg of the prosthesis with respect to each other.

When the piston rod 6 is moved into and withdrawn from the cylinder 1, hydraulic fluid will be pressed between the two second chambers 14 and 16 through the connecting line 20. These chambers are not completely filled with hydraulic fluid since the volumetric changes therein as a result of the movement of the piston rod 6, as opposed to the volumetric changes in the two first chambers 13 and 15, are not equally great (since the piston rod 6 occupies part of the volume of the second chamber 14 of the first cylinder part 3), and a lower degree of filling therefore is required to permit moving the piston rod 6. The hydraulic fluid system 14, 16, 20 is used for lubricating the inner walls of the cylinder 1 also from the outer side of the respective piston 7, 8, i.e. on the side facing the respective end wall 5, 17.

The sealing means 11 consists of a U-gasket which is fixed on the piston 7 and the open portion of which is facing the internal transverse partition 2 and which thus is single-acting in such a manner as to allow a small leakage of hydraulic fluid from the chamber 14 to the chamber 13 when the piston rod 6 is withdrawn from the cylinder 1, while it is completely sealing when the piston 6 is moved into the cylinder 1. When the piston rod 6 is withdrawn from the cylinder 1, the U-gasket thus permits a hydraulic fluid layer adhering to the inner wall of the cylinder part 3 to pass into the chamber 13. In this manner, the reciprocating movement of the piston rod 6 brings about a pumping effect producing a pressure increase in the first chambers 13 and 15 and, thus, ensuring that no pressure decrease, with ensuing cavitation, is obtained. In order that the pressure in the first chambers 13 and 15 should not become too high and produce too unelastic a dampening, the hydraulic device has a third connecting line 21 extending between the first chamber 15 of the second cylinder part 4 and the second chamber 14 of the first cylinder part 3, and a pressure relief valve 22 which is provided in the line 21 and adapted to open this line when the pressure in the two first chambers 13 and 15 reaches a predetermined value.

The sealing means 12 consists of two U-gaskets which are fixed on the piston 8 and are facing in opposite directions and, thus, are completely sealing when the piston rod 6 is moved in both directions.

The second cylinder part 4 has a radial projection 23 with a central through bore 24 having an upper portion which by a conically tapering portion merges into a lower portion of smaller diameter. The central bore 24 is part of the connecting line 21 between the chambers 14 and 15, and its conically tapering portion and lower portion at the same time constitute part of the connecting line 18 between the two first chambers 13 and 15. The central bore 24 is closed at its outer end by a plug 25 screwed in the upper portion thereof. An adjusting screw 26, which is threaded at its upper portion, is screwed in a threaded central opening in the plug 25 and extends with its conical end, forming the above-mentioned throttle means 19, down into the tapering portion of the central bore 24. The throttling action of the device thus is adjustable by means of the adjusting screw 26.

An annular piston 27 provided around the adjusting screw 26 is located on such a level in the central bore 24 that the connection between the chambers 14 and 15 is interrupted. The piston 27 is provided on either side with an O-ring seal 28, 29. Outwardly of the outer O-ring 28, there is provided a washer 30 between which and the plug 25 there is provided a spring 31 balancing the pressure in the first chambers 13 and 15 and maintaining the piston 27 on said level. When the pressure in the first chambers 13 and 15 reaches the above-mentioned predetermined value, the spring 31 has been compressed to such an extent that the piston 27 and the O-ring seal 29 are on such a level that the connection between the chambers 14 and 15 is open. The piston 27, the O-ring seals 28 and 29, the washer 30 and the spring 31 thus constitute said pressure relief valve 22.

In the alternative piston-seal arrangement illustrated in FIG. 2, the piston 7 has an annular flange 7' and 7" at either end. The U-gasket, which in this case is displaceable along the piston 7, abuts at its open portion on the flange 7' against which it is urged by a spring 32, such as a cup spring, which is mounted between the U-gasket and the flange 7". When the pressure in the two first chambers 13 and 15 increases, the U-gasket, while compressing the spring 32, is moved to the right in FIG. 2, whereby a substantially axial channel 33 formed in the circumferential surface of the piston 7 is exposed and provides a communication between the first chamber 13 and the second chamber 14. As a result, there is a pressure decrease in the two first chambers 13 and 15. This pressure decrease proceeds until the spring 32 is capable of returning the U-gasket to its initial position in which the channel 33 is not exposed. Consequently, the spring 32 and the channel 33 have the same function as the pressure relief valve 22 and the connecting line 21 and may replace these.

In both the embodiment according to FIG. 1 and the embodiment according to FIG. 2, the external connecting line 20 may be replaced by an internal connecting line in the form of an axial bore extending from the free end surface of the piston 8 and through the piston rod 6 in order, by a radial bore therein, to open into the second chamber 14. In this case, the substantially axial channel 33 in the embodiment of FIG. 2 may be replaced by a radial bore extending from the circumferential surface of the piston 7 into said axial bore.

What I claim and desire to secure by Letters Patent is:
1. Hydraulic device comprising: a cylinder containing hydraulic fluid and having an internal transverse partition which divides the cylinder into a first cylinder part and a second cylinder part in non-communicable relation through said partition externally of a piston rod; a piston rod extending into said first cylinder part through an end wall thereof and further into said second cylinder part through said transverse partition; a first piston and a second piston mounted on the piston rod said pistons being disposed in said first and said second cylinder part, respectively, and being sealed with respect thereto by sealing means and dividing the interior of the respective cylinder parts into a first chamber between the piston and said transverse partition, and a second chamber between the piston and an end wall of the respective cylinder part; a first connecting line connecting both of said first chambers such that they communicate with each other; throttle means in the first connecting line; a second connecting line connecting both of said second chambers such that they communicate with each other; the hydraulic device being adapted, with said piston rod, to be fixed to a first part, such as the upper leg of a leg prosthesis, and with said cylinder to a second part, such as the lower leg of said leg prosthesis, which is movable with respect to said first part in order to dampen the movements of said two parts in relation to each other; a single-acting type U-gasket sealing means interposed between at least one piston and the cylinder such that an open portion of the U shape faces the transverse partition to permit leakage of hydraulic fluid from the respective second chamber when the piston rod is moved in a direction away from said tranverse partition, and to be completely sealing when the piston rod is moved in the opposite direction; and, connection means provided between one of said first chambers and one of said second chambers; radially extending flanges located at either end of the at least one piston so as to locate the U-gasket therebetween; and, biasing means interposed between the U-gasket and a first of the flanges to bias the U-gasket toward the other flange to form a pressure relief valve means for opening said connection means when the pressure of the hydraulic fluid in said one first chamber exceeds a predetermined value.

2. Hydraulic device as claimed in claim 1 wherein the throttle means is adjustable.

3. Hydraulic device as claimed in claim 2 wherein the throttle means comprises a threaded screw element threadingly engaging a portion of the hydraulic device and having a tapered end portion, such that, as the element is rotated, the throttling effect may be adjusted.

* * * * *